(12) United States Patent
Sicheneder et al.

(10) Patent No.: US 6,946,577 B2
(45) Date of Patent: Sep. 20, 2005

(54) PROCESS FOR THE PRODUCTION OF AMINODIPHENYLAMINES

(75) Inventors: Adolf Sicheneder, Hohenlockstedt (DE); Ulrich Scholz, Mülheim an der Ruhr (DE); Joachim Haider, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/751,314

(22) Filed: Jan. 2, 2004

(65) Prior Publication Data

US 2004/0143139 A1 Jul. 22, 2004

(30) Foreign Application Priority Data

Jan. 7, 2003 (DE) .......................................... 103 00 126

(51) Int. Cl.$^7$ .............................................. C07C 209/10
(52) U.S. Cl. .................................................... 564/406
(58) Field of Search ........................................ 564/406

(56) References Cited

U.S. PATENT DOCUMENTS

| | | | |
|---|---|---|---|
| 4,122,118 A | 10/1978 | George et al. | 260/576 |
| 4,187,248 A | 2/1980 | Merten et al. | 260/576 |
| 4,187,249 A | 2/1980 | Maender et al. | 260/576 |
| 4,665,232 A | 5/1987 | Podder et al. | 564/406 |
| 4,670,595 A | 6/1987 | Podder et al. | 564/406 |
| 4,683,332 A | 7/1987 | Sturm | 564/414 |
| 5,576,460 A | 11/1996 | Buchwald et al. | 564/386 |
| 5,831,128 A | 11/1998 | Beller et al. | 564/405 |
| 5,840,982 A | 11/1998 | Reynolds et al. | 564/423 |
| 6,316,673 B2 | 11/2001 | Giera et al. | 564/423 |
| 2004/0198997 A1 * | 10/2004 | Scholz et al. | 556/13 |

FOREIGN PATENT DOCUMENTS

| | | |
|---|---|---|
| DE | 185663 | 4/1906 |
| DE | 32 47 151 | 6/1984 |
| WO | 02/085838 | 10/2002 |

OTHER PUBLICATIONS

Kirk–Othmer, Encyclopedia of Chemical Technology, $4^{th}$ edition, vol. 3, 1992, pp. 424–456, "Antioxidants".

Ullman's Encyclopedia of Industrial Chemistry, $5^{th\ edition}$, vol. A 3, 1985, pp. 91–111, Peter P. Klemchuk, "Antioxidants".

Tetrahedron Letters, 42, 2001, pp. 4791–4793, Rattan Gujadhur et al, "Formation of aryl–nitrogen bonds using a soluble copper (I) catalyst".

* cited by examiner

*Primary Examiner*—Brian Davis
(74) *Attorney, Agent, or Firm*—Jennifer R. Seng

(57) ABSTRACT

The present invention relates to a process for the production of aminodiphenyl-amines, such as 4-aminodiphenylamine (4-ADPA), by reacting nitrohalogenated benzenes with anilines in the presence of a base as well as a copper-phosphorus complex, followed by hydrogenation of the intermediately formed nitrodiphenyl-amines.

8 Claims, No Drawings

PROCESS FOR THE PRODUCTION OF AMINODIPHENYLAMINES

FIELD OF THE INVENTION

The present invention relates to a process for the production of aminodiphenyl-amines, such as 4-aminodiphenylamine (4-ADPA), by reacting nitrohalogenated benzenes with anilines in the presence of a base as well as a copper-phosphorus complex, followed by hydrogenation of the intermediately formed nitrodiphenyl-amines.

BACKGROUND OF THE INVENTION 4-aminodiphenylamine (4-ADPA) is an important precursor in the synthesis of anti-ageing agents and stabilisers in the rubber and polymer industry (Kirk-Othmer, Encyclopedia of Chemical Technology, $4^{th}$ Edition, 1992, Vol. 3, pp. 424–456; Ullmann's Encyclopedia of Industrial Chemistry, $5^{th}$ Edition, Vol. A3, 1985, pp. 91–111).

4-ADPA may be produced by various methods. One possible way of producing 4-ADPA is the two-stage reaction of aniline or aniline derivatives with p-nitro-chlorobenzene in the presence of an acid acceptor or a neutralising agent, and optionally in the presence of a catalyst. The production according to this method is described for example in DE-A 3 246 151, DE-A 3 501 698, DE-A 185 663, U.S. Pat. Nos. 4,670,595, 4,187,249, 4,683,332 and 4,187,248. The first stage is generally carried out with copper catalysts, and the second stage with metal components different therefrom, for example nickel (see for example U.S. Pat. No. 5,840,982). Reactions of for example also halogenated nitrobenzenes with amines in the presence of palladium catalysts are described in U.S. Pat. No. 5,576,460 and EP-A 846 676.

A disadvantage of the production method identified above using copper catalysis is the comparatively poor selectivity of the reaction with regards to the formation of the desired diarylamine. The 5–15% of the triarylamine that is normally formed results in an increased distillative expenditure for the purification of the end product, as well as in economic drawbacks due to increased consumption of the valuable component halogenated nitrobenzene, since two equivalents of halogenated nitrobenzene are consumed per one equivalent of triarylamine that is formed. In addition the disposal of the byproduct represents an ecological problem.

It was therefore desirable to provide a process for the production of amino-diphenylamines that starts from anilines and leads, by reaction with corresponding nitrohalogenated benzenes, to nitrodiphenylamines followed by reduction of the intermediate product that is formed in relatively high yield and with reduced formation of the triarylamine product, to the desired aminodiphenylamines.

Venkataraman et al. [Tetrahedron Letters, 2001, 42, 4791–4793] were able to show that the use of a preformed complex of copper dibromide and triphenyl-phosphine produces a novel catalyst that catalyses the addition of aryl halides to secondary aromatic amines with the formation of triarylamine.

The addition of aryl halides to primary amines does not, however, as shown in a comparison example, provide any significant advantages compared to the Cu/Cs catalyst system known from DE 3 246 151 A1.

It was therefore surprising that the use of certain copper-phosphorus complexes in the reaction of nitrohalogenated benzenes with anilines yields only very small amounts of the undesired triarylamine as byproduct. Also surprising was the raised catalytic activity of these complexes with respect to the formation of nitrodiphenylamines.

SUMMARY OF THE INVENTION

The present invention accordingly provides a process for the production of aminodiphenylamines, which includes reacting nitrohalogenated benzenes with anilines in the presence of a base and a catalyst and the intermediately formed nitrodiphenylamines are then hydrogenated in a conventional manner, wherein as catalyst copper-phosphorus complexes of the general formula

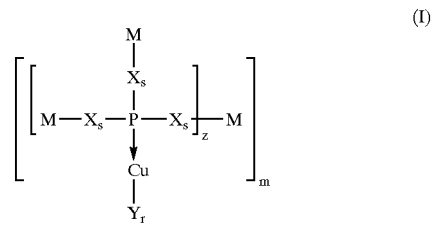

(I)

are used, in which

X may be identical or different and denotes O, NH, S or $C_nH_{2n}$, with the proviso that n may be arbitrarily chosen for each X and denotes 0, 1, 2 or 3, M may be identical or different and denotes $C_6$–$C_{18}$-aryl, $C_1$–$C_{19}$-alkyl, $C_7$–$C_{19}$-aralkyl or denotes heteroaryl with 1 to 3 heteroatoms and 6 to 19 C atoms, wherein two or more radicals M may arbitrarily be bridged by a covalent bridge or by an alkylidene bridge containing 1 to 4 carbon atoms, Y denotes halogen or a trifluoroacetyl, trifluoromethanesulfonyl, nonafluorobutanesulfonyl, cyanide, acetyl, an optionally fluorinated acetylacetonyl, a nitrate, arylsulfonyl, oxinate, phosphate, carbonate or tetrafluoroborate radical, z denotes 1, 2 or 3, m denotes integers from 1 to 6, r denotes 0, 1 or 2, and s denotes 0 or 1.

In the general formula (I) X preferably denotes a methylidene or ethylidene group, M denotes a phenyl, biphenyl or naphthyl radical, or denotes a heteroaryl radical with 1 to 3 nitrogen atoms and 5 to 12 carbon atoms, in particular a pyridyl or quinolinyl radical, or denotes a $C_2$–$C_{12}$-alkyl radical that may also be branched, such as a methyl, ethyl, n-propyl, i-propyl, n-butyl, tert.-butyl, cyclopentyl or cyclohexyl radical.

Y denotes chlorine, bromine or iodine or denotes a trifluoromethylsulfonyl or an acetonyl radical.

In the above formula (I) z preferably denotes the numbers 1 or 2, m denotes the numbers 1, 2 or 3, r denotes the numbers 1 or 2, and s denotes 0.

The above general formula (I) includes copper-phosphine complexes as well as copper-phosphonite complexes and also copper-phosphite complexes.

DETAILED DESCRIPTION OF THE INVENTION

Suitable copper-phosphine complexes are for example those whose phosphine ligands are based on compounds such as tri-o-tolylphosphine, tricyclohexyl-phosphine, tricyclopentylphosphine, tri-t-butylphosphine, tri-n-butylphosphine, bisdiphenylphosphinoethane, bisdiphenylphosphinopropane, bisdiphenyl-phosphinobutane, bisdicyclohexylphosphinoethane, bisdiphenylphosphino-ferrocene, 5,5'-dichloro-6,6'-dimethoxybiphenyl-2,2'-di-yl-bis-diphenyl-phosphine, bis-4,4'-dibenzofuran-3,3'-yl-bisdiphenylphosphine, 1,1'-bisdiphenylphosphinodiphenyl ether, bis(2-dicyclohexylphosphino)-2'-(N,N-dimethylamino)biphenyl, 2-(dicyclohexylphosphino)-biphenyl, 2-(dicyclohexylphosphino)-2'-methylbiphenyl, 2-(di-tert.-butylphosphino)biphenyl or 2-(bisdiphenylphosphino)-binaphthyl, preferably 2-(di-tert.-butylphosphino)biphenyl or 2-(dicyclohexylphosphino)biphenyl, and in which the copper has the valency 0, +I or +II, and the complexing copper compounds are based on copper oxides, copper halides, copper cyanides and copper acetates, copper acetylacetonates in fluorinated or non-fluorinated form, copper nitrates, copper trifluoromethanesulfonates, copper aryl sulfonates, copper oxinates, copper phosphates, preferably based on copper(I) chloride, copper(I) bromide, copper(I) iodide, copper(II) bromide, copper(II) chloride, copper(II) acetate, copper(I) oxide or copper(II) acetylacetonate, as well as copper powders, in particular based on copper(I) chloride, copper(I) bromide or copper(I) trifluoromethanesulfonate.

Preferred copper-phosphine complexes are those with 2-(di-tert.-butylphosphino)biphenyl ligands and 2-(dicyclohexylphosphino)biphenyl ligands and copper(I) bromide or copper trifluoromethanesulfonate as copper or copper compound.

In the process according to the invention there are for example used as copper-phosphonite complexes those that contain as phosphonite ligands compounds such as 1,1'-biphenyl-2-yl-dialkyl phosphonites, preferably 1,1'-biphenyl-2-yl-dicyclohexyl phosphonite and 1,1'-biphenyl-2-yl-di-tret.-butyl phosphonite, 3-[(diisopropyl-phosphino)oxy]phenyl diisopropyl phosphonite, 3-[(di-tret.-buylphosphino)oxy]phenyl di-tert.-butyl phosphonite, 3-[(diphenylphosphino)oxy]phenyl diphenyl phosphonite or 3-[(dicyclohexylphosphino)oxy]phenyl dicyclohexyl phosphonite, more preferably 3-[(diisopropylphosphino)oxy]phenyl diisopropyl phosphonite and that are based on the aforementioned copper compounds or on copper itself.

Suitable copper-phosphite complexes are for example those that are based on the following phosphites and on the aforedescribed copper compounds or copper itself.

Thus, as copper-phosphite complexes there may be mentioned those that carry as phosphite triphenyl phosphite, tris(2,4-di-tert.-butylphenyl) phosphite, 1,1'-binaphthyl-2,2'-di-yl)-isopropyl phosphite or 2,4,8,10-tetratert.-butyl-6-phenoxy-12H-dibenzo[d,g]-[1,3,2]dioxaphosphocine.

Preferred are copper-phosphite complexes that carry as phosphite triphenyl phosphite or tris(2,4-di-tert.-butylphenyl) phosphite.

The aforementioned copper-phosphorus complexes may be used individually as well as in arbitrary mixtures with one another. The desired mixture composition may be determined by appropriate preliminary tests.

The copper-phosphorus complexes of the formula (I) to be used according to the present invention are prepared by reacting phosphorus compounds of the formula (II)

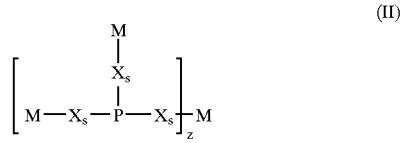
(II)

with copper compounds of the formula (III)

wherein M, X, Y, s, z and r have the meanings given in the formula (I).

To prepare the copper-phosphorus complexes of the general formula (I) the starting products of the general formula (II) and of the general formula (III) are used in such a molar ratio that the desired target complex of the general formula (I) is formed. In general the molar ratio of the phosphorus compounds of the formula (II) to the copper compounds of the formula (III) is about 40:1 to 0.5:1, preferably 5:1 to 1:1, more preferably 4:1 to 1:1.

The copper-phosphorus complexes may be prepared separately in an inert organic solvent suitable for this purpose, such as tetrahydrofuran, diethyl ether, toluene, xylene, chloroform, dichloromethane, methanol and/or ethanol.

The most appropriate amount of solvent to be used may be determined by appropriate preliminary tests.

The preparation of the copper-phosphorus complexes from the described starting compounds of the formulae (II) and (III) is carried out by simple mixing of the two starting compounds in solution at room temperature.

It is also possible to prepare the copper-phosphorus complexes in situ during the reaction of the nitrohalogenated benzenes with anilines.

This means that the copper-phosphorus complexes may be added separately to the reaction of nitrohalogenated benzenes with anilines or, as already mentioned, may ultimately be formed in situ during the overall reaction.

The amount of copper-phosphorus complexes to be used is normally 0.02 mole % to 10 mole %, preferably 0.1 mole % to 3 mole %, based on the amount of nitrohalogenated benzenes used.

The nitrohalogenated benzenes used in the process according to the present invention are those in which the nitro group is preferably in the para position relative to the halogen atom. Suitable halogen atoms are for example fluorine, chlorine or bromine, preferably fluorine or chlorine. Instead of the nitro-halogenated benzenes there may also be used other activated nitrobenzenes, for example those that contain a trifluoromethanesulfonic acid ester substituent or a nonafluorobutanesulfonic acid ester substituent or a carbamate substituent.

Obviously the nitrohalogenated benzenes as well as the other activated nitro-benzenes may be singly or multiply substituted, for example by alkyl radicals, preferably those containing 1 to 12 C atoms, in particular 1 to 4 C atoms. Obviously the position of the nitro group relative to the halogen atoms or to the activated groups may also be other than in the para position, for example in the ortho or meta position.

The following may be mentioned for example as nitrohalogenated benzenes: 4-nitro-2-methylchlorobenzene, 4-nitro-3-methylfluorobenzene, 4-nitrochlorobenzene, 3-nitro-chlorobenzene or 2-nitrochlorobenzene; 4-nitrochlorobenzene is preferred.

As activated nitrobenzenes there may be mentioned for example: 4-nitrophenyltrifluoromethanesulfonic acid ester, 4-nitrophenylnonafluorobutanesulfonic acid ester or 4-nitrophenyl carbamate; 4-nitrophenyltrifluoromethylsulfonic acid ester is preferred.

Anilines that may be used in the process according to the present invention include, apart from aniline itself, also o-, m- and p-substituted anilines. The following are suitable as substituents: branched or unbranched $C_1$–$C_{29}$-alkyl or $C_1$–$C_{29}$-alkenyl radicals, acyl, alkylthio, alkylamino or alkoxy radicals with 1 to 29 carbon atoms, carboxylic acid esters with 1 to 29 carbon atoms in the carboxylic acid part and 1 to 29 carbon atoms in the ester part, as well as sulfonic acid radicals with 1 to 9 carbon atoms in the ester part. The following, preferably, may be mentioned as substituents: branched or unbranched alkyl, alkenyl or alkylthio radicals with the aforementioned numbers of carbon atoms, for example octyl, decyl, dodecyl, oleyl, myristyl or stearyl radicals.

The following may be mentioned as substituted anilines: vinylaniline, 4-tert.-butylaniline, p-anisidine, o-anisidine, o-toluidine, p-toluidine, anthranilic acid methyl ester, o-aminobenzonitrile, p-aminobenzonitrile and 4-ethylaniline. Aniline is preferably used.

According to the process of the present invention 1 to 10 moles, preferably 1.5 to 8 moles, more preferably 2 to 6 moles of the corresponding aniline are used per mole of nitrohalogenated benzene or per mole of activated nitrobenzene.

Bases that are used in the process according to the present invention include alkali metal and/or alkaline earth metal carbonates, alcoholates, phosphates, fluorides and/or hydroxides, in which connection there may be mentioned potassium carbonate, sodium carbonate, caesium carbonate, caesium hydrogen carbonate, sodium methanolate, potassium tert.-butylate, potassium amylate, caesium fluoride, potassium phosphate and barium hydroxide. Potassium carbonate, sodium carbonate, caesium carbonate and/or caesium hydrogen carbonate are preferably used.

Potassium carbonate is more preferably used.

The bases may be used in sub-stoichiometric amount or also in an excess of up to ten times the equivalent amount with respect to the nitrohalogenated benzene. The bases are particularly preferably used in a 0.3 to 2 equivalent amount referred to nitrohalogenated benzene.

It is advantageous for the process according to the present invention if the bases that are used are pretreated by grinding and/or drying.

The grinding may be carried out in the process according to the present invention in for example commercially available mills. The grinding process produces a dramatic enlargement of the specific surface, leading to a significant increase in the conversion. In many cases an enlargement of the specific surface by a factor of 10 to 20 can be observed due to the grinding.

After the grinding the specific surfaces of the bases are ca. 0.1 to 10 m$^2$/g, preferably 0.2 to 1 m$^2$/g (BET).

On account of the pronounced hygroscopic properties of the bases used in the process according to the present invention, the phosphates and carbonates tend to exhibit a more or less significant absorption of atmospheric constituents such as water and carbon dioxide. Starting at an absorption rate of 30 wt. % of atmospheric constituents, a marked influence on the conversions to be achieved can be detected. For this reason, in addition to the grinding it may be desirable to dry the bases.

Depending on the nature of the base that is used, the bases are dried for example by heating under a reduced pressure of ca. 0.01 to 100 mbar for several hours at temperatures of 50° C. to 200° C., preferably 100° C. to 160° C.

The first stage of the process according to the invention may be carried out at temperatures in the range from 20° C. to 250° C., preferably at temperatures of 110° C. to 210° C. The reaction temperatures depend on the nature of the starting products, the catalyst and the bases that are used.

The process according to the present invention may be carried out in the presence as well as in the absence of a suitable solvent. Suitable solvents include for example inert organic hydrocarbons such as xylene and toluene. In addition the aromatic amines that are used may act as solvents.

In the process according to the present invention the water of reaction that is possibly formed may be removed, if desired, similarly to DE-A 2 633 811 and DE-A 3 246 151, by distillation, for example with the aid of a suitable entrainment agent.

The amount of solvents to be used may easily be determined by appropriate preliminary tests.

The process according to the present invention may be carried out according to conventional methods in a continuous or batchwise manner.

The reduction and hydrogenation of the resultant nitrodiphenylamines to form the aminodiphenylamines may be carried out with the aid of a reducing agent such as hydrogen, optionally in the presence of the copper already present, and optionally with the addition of a suitable inert catalyst support.

It is also possible to carry out the hydrogenation in the presence of additional hydrogenation catalysts, such as those based on nickel, palladium or platinum, optionally with the use of a suitable catalyst support.

Suitable materials for use as catalyst support include all technically conventional catalyst supports based on carbon, oxides, carbides or salts in various application forms. Examples of carbon-containing supports are coke, graphite, carbon black or activated carbons. Examples of oxidic catalyst supports are $SiO_2$ (natural or synthetic silicic acid, quartz), $Al_2O_3$ ($\alpha$-, $\gamma$-$Al_2O_3$), argillaceous earths, natural or synthetic alumosilicates (zeolites), layer silicates such as bentonite and montmorillonite, $TiO_2$ (rutile, anatase), $ZrO_2$, MgO or ZnO. Examples of carbides and salts are SiC, $AlPO_4$, $BaSO_4$, $CaCO_3$. In principle synthetic materials may be used as well as supports derived from natural sources such as pumice stone, kaolin, bleaching earths, bauxites, bentonites, kieselguhr, asbestos or zeolites.

Activated carbons and Si-, Al-, Mg-, Zr- and Ti-containing materials are preferably used as support materials.

Activated charcoal is more preferred.

The hydrogenation may also be carried out by other reduction methods such as are known to the person skilled in the art and described for example in "Reductions in Organic Chemistry, Second Edition, ACS Monograph 188".

The hydrogenation can be carried out at temperatures of 0° C. to 200° C., preferably 40° C. to 150° C. and pressures of (hydrogen pressure) 0.1 to 150 bar, preferably 0.5 to 70 bar and more preferably 1 to 50 bar.

The corresponding aminodiphenylamines are obtained by the process according to the present invention with a high selectivity (>95%) and in yields of up to 97% of theory.

The present invention also provides for the production of nitrodiphenylamines, which are obtained as intermediates in the reaction according to the present invention of nitrohalogenated benzenes with anilines in the presence of a base and a copper-phosphorus complex of the general formula (I).

The invention is further illustrated but is not intended to be limited by the following examples in which all parts and percentages are by weight unless otherwise specified.

EXAMPLES

Preparation of the Copper-phosphine Complexes

Example 1

Preparation of bis(2-(di-tert.-butylphosphino)biphenyl copper(I) bromide 50 ml of degassed, anhydrous methanol were heated at reflux temperature, and 2.36 g (7.9 mmole) of 2-(di-tert.- butylphosphino)biphenyl were slowly added to the methanol until the phosphine compound had completely dissolved. 0.59 g (2.6 mmole) of copper(II) bromide was then added in portions to the solution. After addition of the copper bromide the solution was heated for a further 15 minutes at reflux temperature and the solution was then cooled. After cooling the solution a precipitate formed that was filtered off and was washed with a small amount of ethanol and diethyl ether and then dried. 0.93 g (1.1 mmole) of the abovementioned compound was obtained. The yield was 80% of theory.

Example 2

Preparation of 3-[(diphenylphosphino)oxy]phenyl diphenyl phosphonite copper(I) chloride 5 g (10.4 mmole) of 3-[(diphenylphosphino)oxy]phenyl diphenyl phosphonite are dissolved in degassed anhydrous dichloromethane in a round-bottom flask and heated to 40° C. 0.35 g of copper(I) chloride (0.35 mmole) is added. After 30 minutes' stirring the solvent is removed in vacuo. The abovementioned compound was obtained.

Example 3

Preparation of dimeric 1,1'-biphenyl-2-yl-dicyclohexyl phosphonite copper(I) chloride 5 g (13.6 mmole) of 1,1'-biphenyl-2-yl-dicyclohexyl phosphonite are dissolved in anhydrous degassed chloroform in a round-bottom flask. 0.45 g (4.5 mmole) of copper (I) chloride is added in a stream of argon and stirred for 6 hours at room temperature. The solvent is removed in vacuo and the residue is taken up in anhydrous ether. The solution is cooled to −78° C., whereupon the product precipitates out.

Example 4

Preparation of dimeric 4-isopropoxydinaphtho[2.1-d:1',2'-f][1,3,2]dioxa-phosphepine copper(I) chloride 5 g (13.4 mmole) of 4-isopropoxydinaphtho[2.1-d:1',2'-f][1,3,2]dioxaphosphepine (rac.-binaphthylisopropyl phosphlte) are dissolved in dichloromethane in a round-bottom flask and 0.44 g (0.45 mmole) of copper(I) chloride is added in a stream of argon. After stirring for 30 minutes the solvent is removed in vacuo.

Example 5

4-NDPA Condensation with Cu-phosphine Catalyst Produced In situ with Cu(I) Bromide as Precursor 288.9 g (3090 mmole) of aniline, 8.16 g (27 mmole) of 2-(di-tert.-butylphosphino)-biphenyl, 3.87 g (27 mmole) of Cu(I) bromide, 83.6 g (605 mmole) of ground potassium carbonate and 157.6 g (1000 mmole) of p-NCB were added while stirring and under a nitrogen atmosphere to a 1000 ml capacity four-necked flask equipped with mechanical stirrer, Vigreux column and water separator (filled with 35 ml of xylene), and the whole was heated to reflux temperature. The initially slight formation of water increased during the course of the reaction and then remained constant at a low level (total ca. 9 ml). The temperature of the reaction mixture rose from an initial value of 189° C. to 200° C. Samples (unfiltered) were taken every 30 minutes and the conversion and the 4-NDPA/triarylamine ratio were determined by HPLC. The experiment was finished after 4.5 hours. A residual p-NCB value of 0.66 wt. % was found (corresponding to 99% conversion of p-NCB), a 4-NDPA content of 41.2 wt. % was found, the 4,4'-dinitrotriphenylamine content was 0.78% and the 4-NDPA/triarylamine ratio was 52:1 (corresponding to 97% of theory of 4-NDPA and a 98% selectivity referred to p-NCB).

Example 6

4-NDPA condensation with preformed $Cu_2Br_2$(2-di-tert.-butylphosphino)-biphenyl)$_2$ catalyst (reduced amount)

3.22 g (3.64 mmole) of $Cu_2Br_2$(2-di-tert.-butylphosphino)-biphenyl)$_2$ were stirred under a 50 l/hour stream of nitrogen at room temperature for 10 minutes in 372 g (3.99 mole) of aniline in a 1000 ml four-necked flask equipped with mechanical stirrer, Vigreux column and water separator (filled with 35 ml of xylene). 157.6 g (1.00 mole) of p-nitrochlorobenzene (abbreviation p-NCB) and 96.6 g (700 mmole) of ground potassium carbonate were then added and heated under reflux. A constant separation of water occurs at the start of refluxing. The temperature of the reaction mixture rose from an initial value of 189° C. to 196° C. After 5 hours samples (unfiltered) of the reaction mixture were taken and the composition was determined by HPLC, the 4-NDPA/triarylamine ratio was also determined by HPLC, and the reaction batch was cooled. A residual p-NCB value of 6.2 wt. % was found (corresponding to 84% conversion), and a 4-NDPA/triarylamine ratio of 59 was found (corresponding to 82.4% 4-NDPA yield and 98% selectivity referred to p-NCB).

Example 7

4-NDPA Condensation with Cu-phosphine Catalyst Formed In situ (Reduced Amount) with Cu(I) Bromide as Precursor 288.9 g (3090 mmole) of aniline, 2.42 g (8.1 mmole) of 2-(di-tert.-butylphosphino)-biphenyl), 1.16 g (8.1 mmole) of Cu(I) bromide, 83.6 g (605 mmole) of ground potassium carbonate and 157.6 g (1000 mmole) of p-NCB were added while stirring and under a nitrogen atmosphere to a 1000 ml four-necked flask equipped with mechanical stirrer, Vigreux column and water separator (filled with 35 ml of xylene) and the contents were heated to reflux temperature. The initially small amount of water formed increased during the course of the reaction and then remained constant at a low level (total ca. 7 ml). The temperature of the reaction mixture rose from an initial value of 189° C. to 198° C. Samples were taken (unfiltered) every 30 minutes and the conversion and the 4-NDPA/triarylamine ratio were determined by HPLC. The experiment was finished after 7 hours. A residual p-NCB value of 4.2 wt. % was found (corresponding to 89% conversion), a 4-NDPA content of 37.2 wt. % was found, a 4,4'-dinitrotriphenylamine content of 1.9% was found and the 4-NDPA/triarylamine ratio was 33 (corresponding to 86% 4-NDPA yield and 97% selectivity referred to p-NCB).

Example 8

4-NDPA Condensation with Cu-phosphine Catalyst Prepared In situ with Cu(I) Triflate Benzene Complex as Precursor 288.9 g (3090 mmole) of aniline, 2.14 g (27 mmole) of copper(II) oxide, 83.6 g (605 mmole) of ground potassium carbonate and 157.6 g (1000 mmole) of p-NCB were placed in a 1000 ml four-necked flask equipped with mechanical stirrer, Vigreux column and water separator (filled with 35 ml of xylene), and then heated to reflux under a stream of nitrogen at a rate of ca. 150 l/hour. Ca 0.4 ml of water separated out after a short time. After ca. 0.5 hour the reaction mixture was cooled to about 120° C. and 4.53 g (8.1 mmole) of Cu(I) trifluoromethanesulfonate benzene complex and 2.42 g (8.1 mmole) of 2-(di-tert.-butylphosphino) biphenyl ligand were added. The reaction mixture was then reheated to the reflux temperature under a gentle stream of nitrogen. Following this, to start with an atypical slight formation of water occurred, which however became increasingly weaker and had completely ceased after 2 hours at the latest (ca. 0.5 ml). The temperature of the reaction mixture rose from an initial value of 188° C. to 196° C. After 6 hours a sample was taken and the composition of the reaction mixture was determined by BPLC. The experiment was then complete. A residual p-NCB value of 4.0 wt. % (corresponding to 89% conversion) was found, a 4-NDPA content of 39.6 wt. % was found, and a 4,4'-dinitrotriphenylamine content of 1.2% and a 4-NDPA/triarylamine ratio of 33 were found (corresponding to 86.4% 4-NDPA yield and 86% selectivity referred to p-NCB).

Example 9
4-NDPA Condensation with Cu-phosphine/phosphite and Phosphonite Catalyst on 10 mmole Scale For the standard system 1.58 g of p-NCB (10 mmole), 0.95 g of potassium carbonate (6.9 mmole), 21.5 mg of Cu(II)O (0.25 mmole), 15.5 mg of CsHCO$_3$ (0.08 mmole) as well as 3.75 g of aniline (40 mmole) are weighed out in 10 ml capacity reaction vessels. In the catalyst screening p-NCB, potassium carbonate and aniline remain unchanged, but 0.25 mmole of the various test catalysts are used. Cooling tubes filled with molecular sieve are attached to the reaction vessels. The reactions are carried out in a stirrer/heating block at 200° C. block temperature and 530 rpm. The reactions were finished after 4 hours. After cooling to about 40° C. a sample was taken in each case and analysed by HPLC.

| Test Catalyst | Conversion (pNCB) [%] | Yield (4-NDPA) [%] | Selectivity 4-NDPA/Triarylamine |
|---|---|---|---|
| Cu(II)O/CsHCO$_3$ (Reference) | 70 | 67 | 22:1 |
| 1,1'-biphenyl-2-yl-di-tert.-butyl phosphine/Cu(II) acetylacetonate | 87 | 85 | 57:1 |
| 1,1'-biphenyl-2-yl-di-tert.-butyl phosphine/Cu(II) acetate | 86 | 85 | 63:1 |
| 1,1'-biphenyl-2-yl-dicyclohexyl phosphonite/copper(I) chloride dimer | 75 | 73 | 39:1 |
| Cu(II)O/2 PP$_{H3}$ (comparison example*) | 50 | 48 | 25:1 |

*)analogous to Venkataraman et al. [Tetrahedron Letters, 2001, 42, 4791–4793]

Comparison Example 1 (Analogous to DE 3 246 151 A1)
4-NDPA Condensation with Cu(II)O-/Cs Catalyst 288.9 g (3090 mmole) of aniline, 2.44 g (12.6 mmole) of caesium hydrogen carbonate, 2.14 g (27 mmole) of copper (II) oxide, 83.6 g (605 mmole) of ground potassium carbonate and 157.6 g (1000 mmole) of p-NCB were added to a 1000 ml capacity four-necked flask equipped with mechanical stirrer, Vigreux column and water separator (filled with 35 ml of xylene), and the reaction mixture was heated under reflux. At the same time, only a gentle stream of nitrogen was adjusted in order to maintain the inert gas atmosphere. Separation of water commenced starting from ca. 189° C. and continued during the course of the reaction. The reaction temperature rose until the end of the reaction—after 5.5 hours—to ca. 203° C. The composition of the reaction mixture was determined by HPLC. A residual p-NCB value of 0.1 wt. % (P-NCB conversion >99%) was found, a 4-NDPA content of 44.8 wt. % and a 4,4'-dinitrotriphenylamine content of 2.1% were found, and a 4-NDPA/triarylamine ratio of 21 was found (corresponding to 87.5% of theoretical yield of 4-NDPA and 88% selectivity referred to p-NCB).

Comparison Example 2 (Analogous to DE 3 246 151 A1)
4-NDPA Condensation with Reduced Amount of Cu(II)O-/Cs Catalyst 288.9 g (3090 mmole) of aniline, 733 mg (3.78 mmole) of caesium hydrogen carbonate, 642 mg (8.1 mmole) of copper(II) oxide, 83.6 g (605 mmole) of ground potassium carbonate and 157.6 g (1000 mmole) of 4-nitrochlorobenzene were added to a 1000 ml capacity four-necked flask equipped with mechanical stirrer, Vigreux column and water separator (filled with 35 ml of xylene), and the reaction mixture was heated under reflux. At the same time, only a gentle stream of nitrogen was adjusted in order to maintain the inert gas atmosphere. Separation of water commenced starting from ca. 189° C. and continued during the course of the reaction. The reaction temperature rose until the end of the reaction—after 5 hours—to ca. 201° C. The composition of the reaction mixture was determined by HPLC.

A residual p-NCB value of 12.5 wt. % was found (corresponding to 63% conversion of p-NCB ), a 4-NDPA content of 22.6 wt. % and a 4,4'-dinitrotri-phenylamine content of 1.1 wt. % were found, and a 4-NDPA/triarylamine ratio of 21 was found (corresponding to 60% of theoretical yield of 4-NDPA and 95% selectivity referred to p-NCB).

Example 10
(Preparation of 4-ADPA)

250 ml of water were added to the reaction mixture from Example 8 after cooling to 105° C., the whole was stirred for 15 minutes at 80° C. and then transferred to a separating funnel After completed phase separation 5 ml of KOH, 25 ml of saline solution (from the aqueous phase of the condensation) and 4.5 g of Raney nickel were added to the separated organic phase (500 ml) and transferred to a hydro-genation autoclave and hydrogenated for 400 minutes at a hydrogen pressure of 10 bar, a temperature of 140° C. being reached. Gas chromatography investigations showed a 99% yield of 4-aminodiphenylamine (referred to the 4-nitrodiphenyl-amine employed).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:
1. Process for the production of aminodiphenylamines comprising the steps of reacting nitrohalogenated benzenes with anilines in the presence of a base and a catalyst, wherein the catalyst is copper-phosphorus complexes of the general formula
wherein

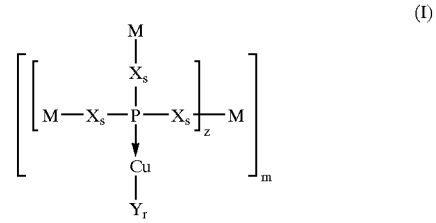

(I)

X may be identical or different and denotes O, NH, S or $C_nH_{2n}$, with the proviso that n may be arbitrarily chosen for each X and denotes 0, 1, 2 or 3, M may be identical or different and denotes $C_6$–$C_{18}$-aryl, $C_1$–$C_{19}$-alkyl, $C_7$–$C_{19}$-aralkyl or denotes heteroaryl with 1 to 3 heteroatoms and 6 to 19 C atoms, wherein two or more radicals M may arbitrarily be bridged by a covalent bridge or by an alkylidene bridge containing 1 to 4 carbon atoms, Y denotes halogen or a trifluoroacetyl, trifluoromethanesulfonyl, nonafluorobutanesulfonyl, cyanide, acetyl, an optionally fluorinated acetylacetonyl, a nitrate, arylsulfonyl, oxinate, phosphate, carbonate or tetrafluoroborate radical, z denotes 1, 2 or 3, m denotes integers from 1 to 6, r denotes 0, 1 or 2, and s denotes 0 or 1, wherein intermediately formed nitrodiphenylamines are hydrogenated.

2. The process according to claim 1, wherein the copper-phosphorus complexes are prepared by reacting phosphorous compounds of the formula (II)

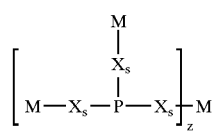
(II)

with copper compounds of the formula (III)

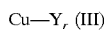 (III)

wherein M, X, Y, s, z and r have the meanings as formula (I).

3. The process according to claim 2, wherein formula (I) is a copper-phosphine complex, a copper-phosphonite complex or a copper-phosphite complex.

4. The process according to claim 1, wherein the nitro-halogenated benzenes are selected from the group consisting of 4-nitro-2-methylchlorobenzene, 4-nitro-3-methylfluorobenzene, 4-nitrochlorobenzene, 3-nitro-chlorobenzene or 2-nitrochlorobenzene, 4-nitrochlorobenzene, 4-nitrophenyl-trifluoromethanesulfonic acid ester, 4-nitrophenylnonafluorobutane-sulfonic acid ester, 4-nitrophenyl carbamate and 4-nitrophenyltrifluoromethylsulfonic acid ester.

5. The process according to claim 1, wherein the aniline is a o-, m- or p-substituted aniline.

6. The process according to claim 5, wherein the substituted aniline is selected from the group consisting of vinylaniline, 4-tert.-butylaniline, p-anisidine, o-anisidine, o-toluidine, p-toluidine, anthranilic acid methyl ester, o-aminobenzonitrile, p-aminobenzonitrile and 4-ethylaniline.

7. The process according to claim 1, wherein the base is selected from the group consisting of alkali metal, alkaline earth metal carbonate, alcoholate, phosphate, fluoride, hydroxide and mixture thereof.

8. The process according to claim 7, wherein the base is selected from the group consisting of potassium carbonate, sodium carbonate, caesium carbonate, caesium hydrogen carbonate, sodium methanolate, potassium tert.-butylate, potassium amylate, caesium fluoride, potassium phosphate and barium hydroxide.

* * * * *